US005466248A

United States Patent [19]

Whitson-Newman

[11] Patent Number: 5,466,248

[45] Date of Patent: Nov. 14, 1995

[54] FOOT GHOST ENDER

[76] Inventor: Jayne C. Whitson-Newman, 121 New St., Hellertown, Pa. 18055

[21] Appl. No.: 298,853

[22] Filed: Aug. 31, 1994

[51] Int. Cl.[6] .......... A61N 5/06

[52] U.S. Cl. .......... 607/88; 607/91; 607/94

[58] Field of Search .......... 607/88, 90–95; 250/504 R

[56] References Cited

U.S. PATENT DOCUMENTS

| | | | |
|---|---|---|---|
| 2,054,332 | 11/1933 | Lower et al. | 607/91 |
| 2,311,415 | 2/1939 | Rouat | 607/91 |

FOREIGN PATENT DOCUMENTS

| | | | |
|---|---|---|---|
| 0265351 | 2/1927 | United Kingdom | 607/91 |

*Primary Examiner*—Lee S. Cohen
*Assistant Examiner*—Robert L. Nasser, Sr.

[57] ABSTRACT

A foot ghost ender comprised of a rounded steel shell having a front, a back, a left sidewall, a right sidewall, an open top, a closed bottom, an inner surface, and an outer surface. An aperture is formed in the right sidewall. An extension is integral with the open top. The extension has an open circular top. A plurality of tanning lamps are secured to the inner surface of the rounded steel shell. An adjustable foot rest is secured to the inner surface of the rounded steel shell. The device also contains a retractable power cord having a first end, and a second end. The first end is received through the aperture formed within the right sidewall of the rounded steel shell. A three-prong polarized plug secured to the first end. A control panel with adjustable timer is secured to the right sidewall of the rounded steel wall. The adjustable timer functions to turn the tanning lamps on and off.

5 Claims, 4 Drawing Sheets

10

12

64

56

FOOT GHOST ENDER

BACKGROUND OF THE INVENTION

1. Field of the Invention

The present invention relates to a foot ghost ender and more particularly pertains to tanning the user's feet and ankles with a foot ghost ender.

2. Description of the Prior Art

The use of tanning apparatuses is known in the prior art. More specifically, tanning apparatuses heretofore devised and utilized for the purpose of tanning the body are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,740,707 to Thaw discloses a portable tanning unit.

U.S. Pat. No. 4,989,600 to Collier discloses a tanning pod.

U.S. Pat. No. Des. 296,131 to James discloses the design of a tanning booth.

U.S. Pat. No. 5,234,710 to Dutta et al. discloses the fluorescent suntanning lamps.

U.S. Pat. No. 5,086,769 to Vianello et al. discloses a tanning chair.

While these devices fulfill their respective, particular objective and requirements, the aforementioned patents do not describe a foot ghost ender that tans the user's feet and ankles.

In this respect, the foot ghost ender according to the present invention substantially departs from the conventional concepts and designs of the prior art, and in doing so provides an apparatus primarily developed for the purpose of tanning the user's feet and ankles.

Therefore, it can be appreciated that there exists a continuing need for a new and improved foot ghost ender which can be used for tanning the user's feet and ankles. In this regard, the present invention substantially fulfills this need.

SUMMARY OF THE INVENTION

In the view of the foregoing disadvantages inherent in the known types of tanning apparatuses now present in the prior art, the present invention provides an improved foot ghost ender. As such, the general purpose of the present invention, which will be described subsequently in greater detail, is to provide a new and improved foot ghost ender and method which has all the advantages of the prior art and none of the disadvantages.

To attain this, the present invention essentially comprises a rounded steel shell having a front, a back, a left sidewall, a right sidewall, an open top, a closed bottom, an inner surface, and an outer surface. An aperture is formed in the right sidewall. An extension is integral with the open top. The extension has an open circular top. A soft cuff is secured to the open circular top. A molded rubber top is secured to the soft cuff. The molded rubber top has a plurality of sections that function to receive a foot. A plurality of rubber ribs are secured to the outer surface of the closed bottom of the rounded steel shell. The rubber ribs function to prevent the rubber steel shell from sliding on a floor. A plurality of tanning lamps are secured to the inner surface of the rounded steel shell. At least one lamp needs to be secured to each of the front, the back, the right sidewall, and the left sidewall.

An intermediate base is secured to the inner surface of the rounded steel shell parallel to the closed bottom and above the aperture formed in the right sidewall. An adjustable foot rest is secured to the inner surface of the rounded steel shell. The device contains a pressure activated toggle switch having a first end and a second end. The first end is secured to the adjustable foot rest. The second end is secured to the intermediate base. The pressure activated toggle switch electrically cooperates with the plurality of tanning lamps. The device also contains a retractable power cord having a first end, a second end, and an intermediate extent therebetween. The first end is received through the aperture formed within the right sidewall of the rounded steel shell. A three-prong polarized plug is secured to the first end. The second end is electrically secured to the pressure activated toggle switch. The intermediate extent, when inactive, is stored between the closed bottom of the rounded steel shell and the intermediate base. A control panel with adjustable timer is secured to the right sidewall of the rounded steel wall. The adjustable timer functions to turn off the tanning lamps after a preset period of time.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved foot ghost ender which has all the advantages of the prior art tanning apparatuses and none of the disadvantages.

It is another object of the present invention to provide a new and improved foot ghost ender which may be easily and efficiently manufactured and marketed.

It is a further object of the present invention to provide a new and improved foot ghost ender which is of durable and reliable construction.

An even further object of the present invention is to provide a new and improved foot ghost ender which is susceptible of a low cost of manufacture with regard to both materials and labor, and which accordingly is then susceptible of low prices of sale to the consuming public, thereby making such a foot ghost ender economically available to the buying public.

Still yet another object of the present invention is to provide a new and improved foot ghost ender which provides in the apparatuses and methods of the prior art some of the advantages thereof, while simultaneously overcoming some of the disadvantages normally associated therewith.

Even still another object of the present invention is to provide a new and improved foot ghost ender for tanning the user's feet and ankles.

Lastly, it is an object of the present invention to provide a foot ghost ender comprised of a rounded steel shell having a front, a back, a left sidewall, a right sidewall, an open top, a closed bottom, an inner surface, and an outer surface. An aperture is formed in the right sidewall. An extension is integral with the open top. The extension has an open circular top. A plurality of tanning lamps are secured to the inner surface of the rounded steel shell. An adjustable foot rest is secured to the inner surface of the rounded steel shell. The device also contains a retractable power cord having a first end, and a second end. The first end is received through the aperture formed within the right sidewall of the rounded steel shell. A three-prong polarized plug secured to the first end. A control panel with adjustable timer is secured to the right sidewall of the rounded steel wall. The adjustable timer functions to turn the tanning lamps on and off.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
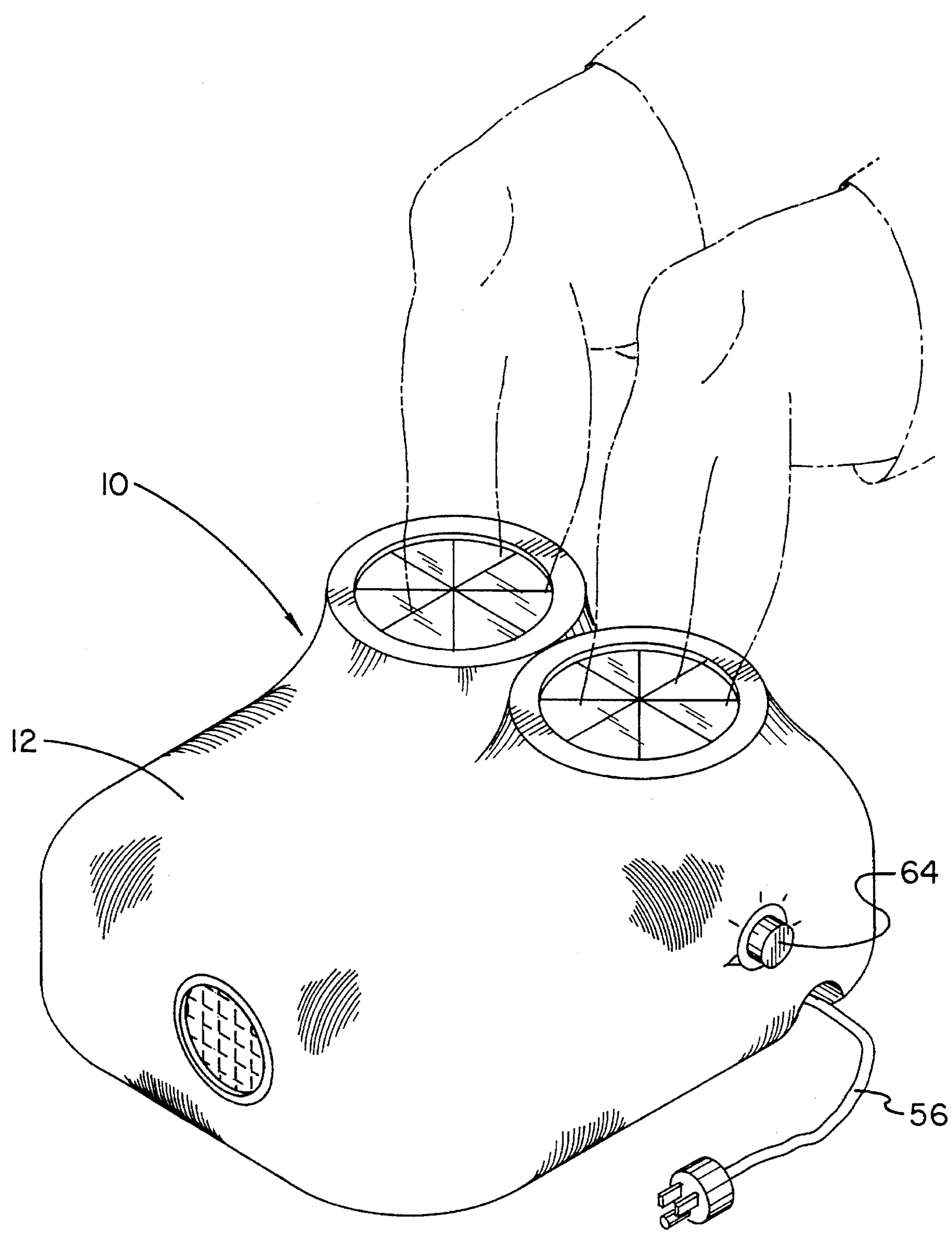
FIG. 1 is a perspective view of the preferred embodiment of the foot ghost ender constructed in accordance with the principles of the present invention.
Figure 2:
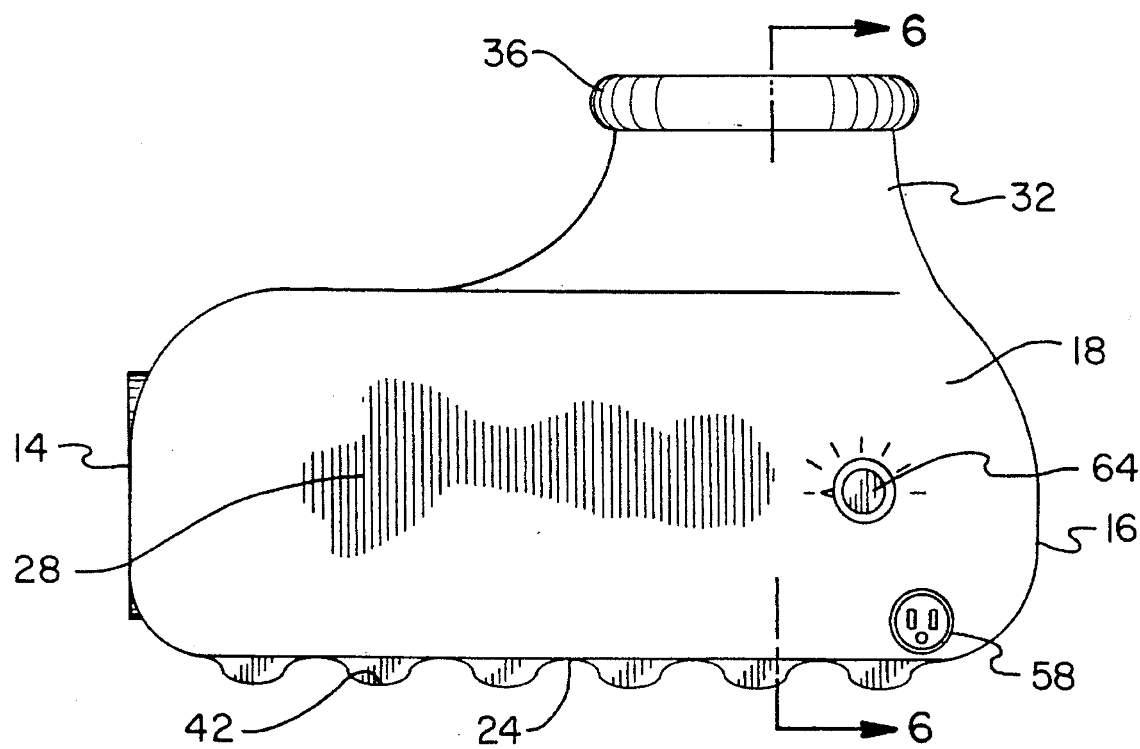
FIG. 2 is a side view of the preferred embodiment in accordance with the principles of the present invention.
Figure 3:
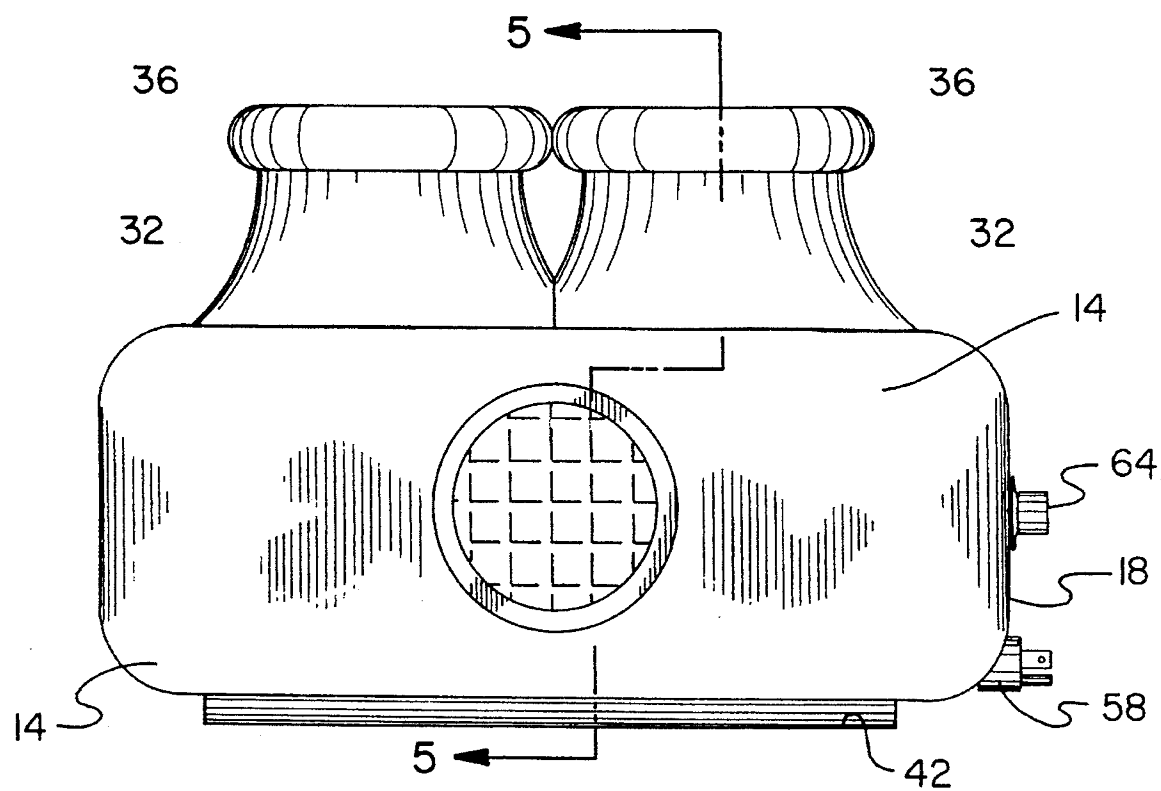
FIG. 3 is a front view of the preferred embodiment of the present invention.
Figure 4:
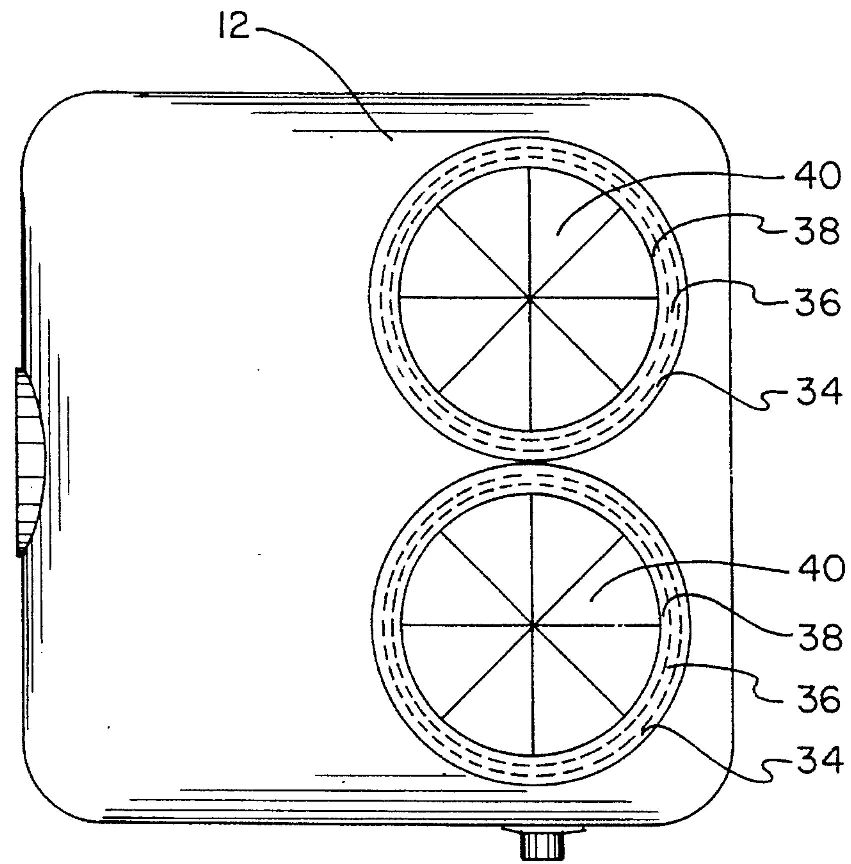
FIG. 4 is an elevational view of the preferred embodiment of the present invention.
Figure 5:
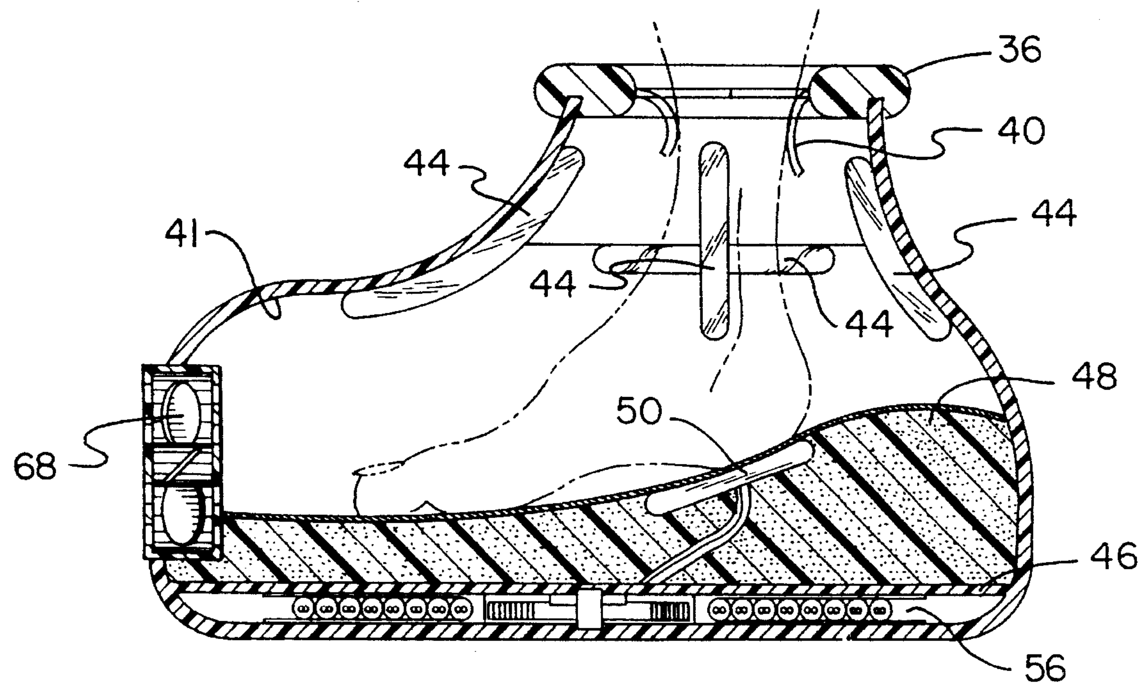
FIG. 5 is a cross-sectional view of the present invention as seen along line 5—5 of FIG. 3.
Figure 6:
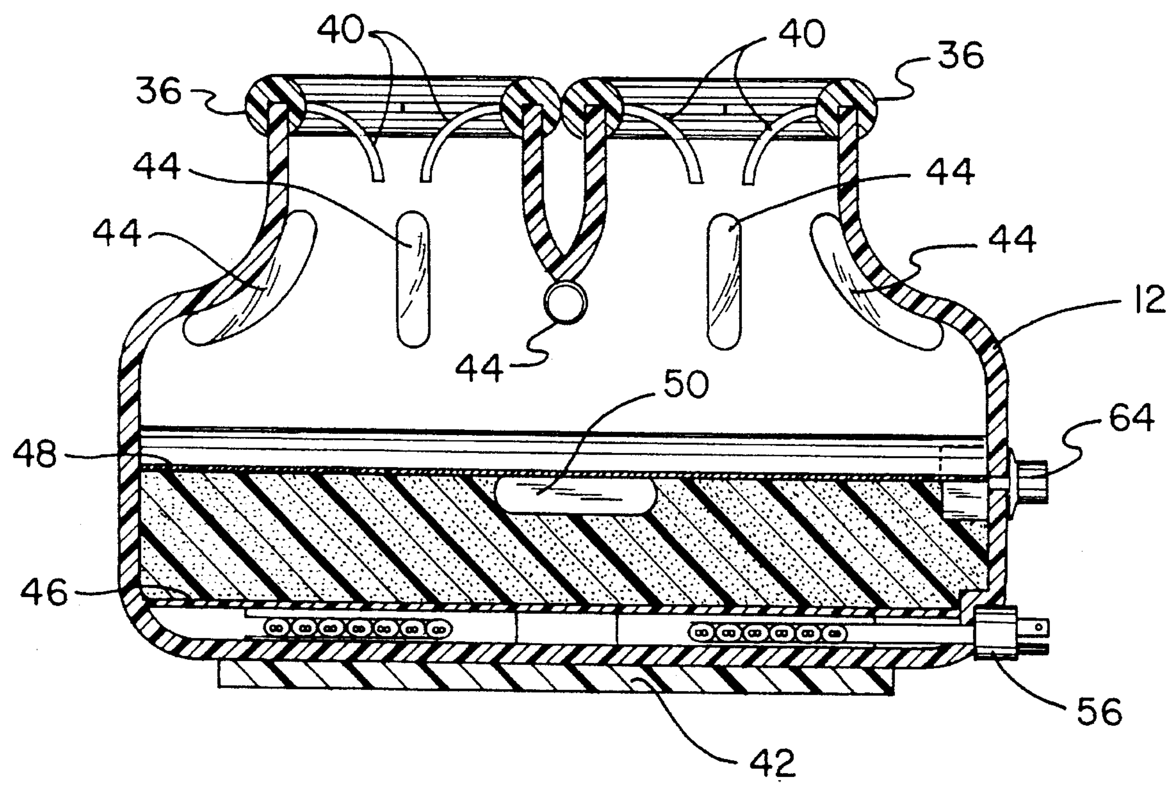
FIG. 6 is a cross-sectional view of the present invention as seen along line 6—6 of FIG. 2.
Figure 7:
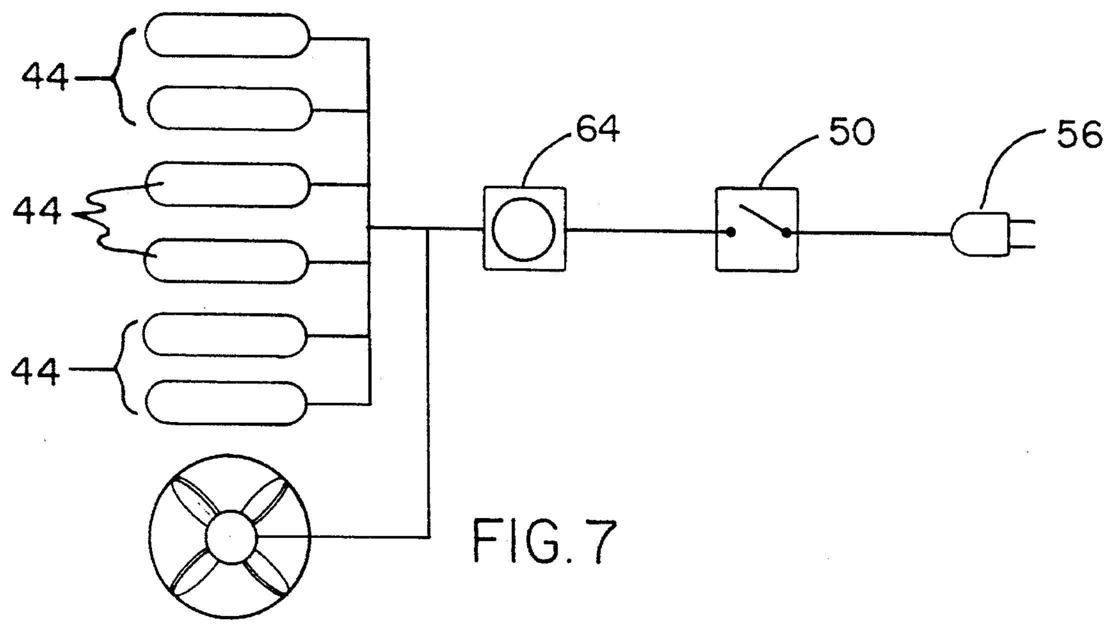
FIG. 7 is a schematic view of the fluorescent bulbs and the plug and the control switch.

With reference now to the drawings, and in particular, to FIG. 1 thereof, the preferred embodiment of the new and improved foot ghost ender embodying the principles and concepts of the present invention and generally designated by the reference number 10 will be described.

Specifically, it will be noted in the various Figures that the device relates to a new and improved foot ghost ender that tans the user's feet and ankles. In its broadest context, the device consists of a rounded steel shell, a plurality of rubber ribs, a plurality of tanning lamps, an intermediate base, an adjustable foot rest, a retractable power cord, and a control panel.

The device 10 contains a rounded steel shell 12 having a front 14, a back 16, a left sidewall 18, a right sidewall 20, an open top 22, a closed bottom 24, an inner surface 26, and an outer surface 28. An aperture 30 is formed in the right sidewall 20. An extension 32 is integral with the open top 22. The extension 32 has an open circular top 34. A soft cuff 36 is secured to the open circular top 34. A molded rubber top 38 is secured to the soft cuff 36. The molded rubber top 38 has a plurality of sections 40 that function to receive a foot. Simply pressing a foot in the plurality of sections 40 will allow the foot to enter the rounded steel shell 12. The inner surface of the shell is preferably provided with a layer 41 of a moisture absorbing material. Such material functions to prevent odors from perspiring feet from exiting the shell.

A plurality of rubber ribs 42 are secured to the outer surface 28 of the closed bottom 24 of the rounded steel shell 12. The rubber ribs 42 function to prevent the rubber steel shell 12 from sliding on a floor.

A plurality of tanning lamps 44 are secured to the inner surface 26 of the rounded steel shell 12. At least one tanning lamp 44 needs to be secured to each of the front 14, the back 16, the right sidewall 18, and the left sidewall 20. By placing a tanning lamp 44 on each of these areas surrounds the foot to be tanned.

An intermediate base 46 is secured to the inner surface 26 of the rounded steel shell 12 parallel to the closed bottom 24 and above the aperture 30 formed in the right sidewall 18.

An adjustable foot rest 48 is secured to the inner surface 26 of the rounded steel shell 12. The device 10 contains a pressure activated toggle switch 50 having a first end 52 and a second end 54. The first end 52 is secured to the adjustable foot rest 48. The second end 54 is secured to the intermediate base 46. The pressure activated toggle switch 48 electrically cooperates with the plurality of tanning lamps 44.

The device 10 also contains a retractable power cord 56 having a first end 58, a second end 60, and an intermediate extent 62 therebetween. The first end 58 is received through the aperture 30 formed within the right sidewall 18 of the rounded steel shell 12. A three-prong polarized plug is secured to the first end 58. The second end 60 is electrically secured to the pressure activated toggle switch 48. The intermediate extent 62, when inactive, is stored between the closed bottom 24 of the rounded steel shell 12 and the intermediate base 46.

A control panel with adjustable timer 64 is secured to the right sidewall 18 of the rounded steel wall 12. The adjustable timer 64 functions to turn off the plurality of tanning lamps 44 after a preset period of time.

Lastly, a cooling fan 68 is secured to the inner surface of the shell. The fan is electrically coupled for the pressure activated toggle switch for Activation & deactivation therewith. Added comfort is thus provided to the user.

A second embodiment of the present invention includes substantially all of the components of the present invention wherein the plurality of tanning lamps 44 that are secured to the inner surface 26 of the rounded steel shell 12 is instead one circular tanning lamp that functions to completely surround a user's foot.

Women who play golf usually wear shorts and skirts. While playing they are out in the open sunlight for sometime, and develop a tan on their legs. However, they also wear golf shoes which keep their feet and ankles from tanning. When they later wear dress shoes, or no shoes, they have untanned "white ghost feet." The present invention is a device that people can use to tan just their feet and ankles, and thus mitigate unsightly ghost feet. It can also be used to tan "ghost hands" that have been protected by gloves.

The present invention is a small portable tanning machine for feet or hands. It is completely enclosed by a rounded steel or aluminum shell, and does not open up. The bottom of the shell has rubber ribs attached to it to keep it from slipping on the floor. The top has a raised hole near one side in which the foot is inserted. A soft cuff surrounds the hole to prevent touching the metal shell. A molded rubber top that is split into a number of sections keeps the light from the tanning lamps from escaping.

Inside the shell are four tanning lamps. These are located under the top in front, on both side, and in back. Alternatively, one circular tanning lamp can be used instead. Electrical power is provided through a power cord with a three-prong polarized plug on its end. The cord retracts inside the base of the shell when not in use. An adjustable footrest is located inside the shell on the bottom. It has a pressure-actuated toggle switch that turns the lamps on and off. An adjustable timer is located on the outside of the shell in front. It starts automatically when the lamps are turned on and will turn the lamps off after a preset period.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A new and improved tanning device for the feet and ankles that tans the users feet and ankles comprising, in combination:

a rounded steel shell having a front, a back, a left sidewall, a right sidewall, an open top, a closed bottom, an inner surface, and an outer surface, an aperture formed in the right sidewall, an extension integral with the open top, the extension having an open circular top, a soft cuff secured to the open circular top, a molded rubber top secured to the soft cuff, the molded rubber top having a plurality of sections functioning to receive a foot;

a plurality of rubber ribs secured to the outer surface of the closed bottom of the rounded steel shell, the rubber ribs functioning to prevent the rubber steel shell from sliding on a floor;

a plurality of tanning lamps secured to the inner surface of the rounded steel shell with at least one lamp secured to each of the front, the back, the right sidewall, and the left sidewall;

an intermediate base secured to the inner surface of the rounded steel shell parallel to the closed bottom and above the aperture formed in the right sidewall;

an adjustable foot rest secured to the inner surface of the rounded steel shell, a pressure activated toggle switch having a first end and a second end, the first end secured to the adjustable foot rest, the second end secured to the intermediate base, the pressure activated toggle switch electrically cooperating with the plurality of tanning lamps;

a retractable power cord having a first end, a second end, and an intermediate extent therebetween, the first end received through the aperture formed within the right sidewall of the rounded steel shell, a three-prong polarized plug secured to the first end, the second end electrically secured to the pressure activated toggle switch, the intermediate extent inactively stored between the closed bottom of the rounded steel shell and the intermediate base; and a control panel with adjustable timer secured to the right sidewall of the rounded steel wall, the adjustable timer functioning to turn off the plurality of tanning lamps after a preset period of time.

2. A new and improved tanning device for the feet and ankles comprising:

a rounded steel shell having a front, a back, a left sidewall, a right sidewall, an open top, a closed bottom, an inner surface, and an outer surface, an aperture formed in the right sidewall, an extension integral with the open top, the extension having an open circular top;

a plurality of tanning lamps secured to the inner surface of the rounded steel shell;

an adjustable foot rest secured to the inner surface of the rounded steel shell;

a retractable power cord having a first end, a second end, and an intermediate extent therebetween, the first end received through the aperture formed within the right sidewall of the rounded steel shell, a three-prong polarized plug secured to the first end;

a control panel with an adjustable timer secured to the right sidewall of the rounded steel wall, the adjustable timer functioning to turn the tanning lamps on and off.

3. The device described in claim 2 and further comprising:

a soft cuff secured to the open circular top of the extension of the rounded steel shell, a molded rubber top secured to the soft cuff, the molded rubber top having a plurality of sections functioning to receive a foot.

4. The device described in claim 3 and further comprising:

an intermediate base secured to the inner surface of the rounded steel shell parallel to the closed bottom and above the aperture formed in the right sidewall.

5. The device described in claim 4 and further comprising:

a pressure activated toggle switch electrically connected to the second end of the retractable power cord, the toggle switch having a first end and a second end, the first end secured to the adjustable foot rest, the second end secured to the intermediate base, the pressure activated toggle switch electrically cooperating with the plurality of tanning lamps.

* * * * *